United States Patent [19]
Martinchek et al.

[11] Patent Number: 6,015,484
[45] Date of Patent: Jan. 18, 2000

[54] DETECTION OF PITTING CORROSION

[75] Inventors: Gregory A. Martinchek, Langhorne; Max R. Yaffe, Maple Glen, both of Pa.

[73] Assignee: Gamry Instruments, Inc., Warminster, Pa.

[21] Appl. No.: 08/978,837

[22] Filed: Nov. 26, 1997

[51] Int. Cl.[7] .................................................. G01N 27/26
[52] U.S. Cl. .......................... 205/775.5; 204/404; 422/53
[58] Field of Search ............................... 205/775.5, 776.5, 205/777, 791.5; 204/404; 422/53; 324/700

[56] References Cited

U.S. PATENT DOCUMENTS

| | | |
|---|---|---|
| 3,766,042 | 10/1973 | Wilson . |
| 4,056,445 | 11/1977 | Gauntt et al. . |
| 4,351,703 | 9/1982 | Winslow . |
| 5,139,627 | 8/1992 | Eden et al. . |

OTHER PUBLICATIONS

U. Bertocci et al, *J. Electrochem. Soc.*, vol. 14, No. 1, (Jan. 1997) pp. 31–43. Noise Resistance Applied to Corrosion Measurement.

*Primary Examiner*—T. Tung
*Assistant Examiner*—Jennifer McNeil
*Attorney, Agent, or Firm*—Elman & Associates

[57] ABSTRACT

Apparatus and methods for monitoring localized or pitting corrosion of metal or other material are described. A probe having a working electrode made of the same material as the material being monitored is located in the same corroding environment as the material being monitored. The electrochemical noise detected between the working electrode and other electrodes is processed to provide an indication of the state of localized corrosion of the material being monitored. An anodic bias voltage is applied to the working electrode. This bias voltage accentuates localized corrosion at the working electrode, improving sensitivity and permitting more accurate evaluation of the electrochemical noise signals.

17 Claims, 6 Drawing Sheets

DETECTION OF PITTING CORROSION

FIELD OF THE INVENTION

This invention concerns improved means for detecting localized corrosion, especially pitting, that takes place on the surface of a metal exposed to a corrosive environment. It provides means for detecting, and for determining the rate and location of, such localized corrosion. The invention provides working electrodes one of which is anodically biased and whereon corrosion occurs thereby generating electrical signals. These signals are detected and analyzed to provide information about the corrosion taking place.

BACKGROUND

When metal components are used for vessels and piping in chemical processing and for structural purposes, it is important to be aware of locations that may be corroding and losing the capabilities for which they were designed. Localized corrosion is most critical in this regard.

Localized corrosion is distinct from general corrosion. As general corrosion takes place, relatively large areas of the surface corrode together, at about a uniform rate. An important kind of localized corrosion is pitting corrosion, which occurs initially in a microscopically tiny area on a material surface and then gets larger and deeper, forming pits in the surface. Electrochemically the area affected becomes consistently anodic in the corrosive medium. Pitting phenomena can be erratic: often a localized anodic reaction starts up and shuts down because of concentration fluctuations in the corrosive medium (or other reasons) and formation of a passive layer on the metal (known as repassivation of the metal surface); such action is known as metastable corrosion and is a precursor of the more damaging fully developed pitting corrosion.

Localized corrosion, particularly pitting, is insidious because material is removed in a concentrated small area that is not easily recognized. One of the most dangerous consequences of pitting corrosion is a leak in a containment vessel such as a tank or pipeline. The leak typically occurs at a pinhole in a wall of the containment vessel. The majority of the wall still has adequate thickness to contain the vessels contents. The resulting leak can be especially dangerous where the contained material is under pressure, at high temperature, or both. The present invention provides a warning system in real time, making the user aware of the extent of localized corrosion before the structure develops pinholes. In extreme cases, pitting can lower the structural integrity of a structure, resulting in a mechanical failure.

Several methods for monitoring localized corrosion are based on electrochemical noise analysis. See U.S. Pat. Nos. 4,575,678 to Hladkey and 5,139,627 to Eden, et al., the disclosures of which are incorporated herein by reference. In the Hladkey patent, fluctuations in the potential between two electrodes are related to corrosion processes. In the Eden, et. al. Patent, a Zero Resistance Ammeter (ZRA) is used to measure current fluctuations between two similar metal electrodes. The ZRA works to match the voltages of the two electrodes while it measures current flow between them. Any current fluctuations are due to "noise" or small statistical variations on the specimen surface. In addition, an electrometer is used to measure potential fluctuations between one of the probes and a reference electrode. The measured values are then filtered and ratioed to produce several reported numbers including a "Noise Resistance" and a "Pitting Index." Any variations are due to localized corrosion since the metal electrodes, being in the same environment at the same electrochemical potential, should have the same general corrosion rate.

A problem with the aforesaid conventional method is that not all of the localized corrosion currents are measured by the ZRA. Usually much of the anodic current originating at the pitting site will be sunk cathodically on the same electrode, never appearing in the ZRA measurement circuit. The present invention provides a means for localizing the reactions on the electrodes, with most of the cathodic reactions occurring on one electrode and the anodic reactions on another. The current measured by the circuit is therefore both larger and a much better measure of the localized corrosion current.

Because the pitting effect itself is localized, the total signal generated by it is small and difficult to detect. To add to the difficulties of measurement, various kinds of electrical noise in or near the structure effectively mask and distort the comparatively weak electric signals that are characteristic of pitting noise. Motors, circuit breakers, switches and radio frequency generators all add to the cacophony tending to obscure the corrosion noise signal. The present invention, with its larger currents, is less susceptible to interference from these external noise sources.

A further problem is that the signal indicative of pitting is defined in the Eden et al. patent as $I_{noise}/I_{mean}$. In this definition $I_{mean}$ can vary with the general corrosion rate. Indeed, if the ZRA is working as designed and the chemical environments of both electrodes are the same, the expected value of $I_{mean}$ is 0, which leads to a measurement singularity. In addition the aforesaid involves extensive interpretation of values, in order to identify the type and rate of corrosion.

SUMMARY OF THE INVENTION

An object of the present invention is to provide an improved monitor for localized corrosion which is straightforward and inexpensive to implement.

Another object of the invention is to provide an improved monitor for localized corrosion that is based on accepted concepts of corrosion science, thereby being acceptable to the corrosion engineering community.

An advantage of the present invention is its capability to predict the onset of pitting corrosion prior to its actual occurrence on the structure being monitored, thereby allowing time for corrective action.

A feature of the present invention is that a multiplicity of sensor arrays may be installed at various locations throughout the structure to allow monitoring in real time and the early detection of localized corrosion.

One embodiment of the present invention comprises a two- or three-electrode probe exposed to a corrosive environment. At least one of the electrodes, the working electrode, has a surface of substantially the same composition and state as a material surface, the corrosion of which is of concern, also exposed to the same environment. A second electrode of the probe, the reference electrode, is used in measuring the voltage of the working electrode.

A novel feature of the present invention is the employment of a biasing circuit. This circuit includes a battery or other power source that anodically biases the working electrode with respect to a cathode. The cathode against which the working electrode is biased may be a discrete electrode (in a three-electrode probe) having a surface of substantially the same composition and state as the material surface, or it may be the material surface itself.

The reference electrode may be an inert metal such as Inconel or platinum, may be a field version of a laboratory reference electrode such as the Ag/AgCl reference electrode, may be any other electrode that has a stable potential in the environment, or may be an electrode having a surface of substantially the same composition and state as the material surface.

The current flowing between the anodically biased electrode and the cathode is measured, and the potential between the anodically biased working electrode and the reference electrode is measured. These two signals either separately or in combination are processed to produce an output indicative of the tendency for the material surface to undergo localized corrosion.

The present invention also contemplates a method according to the preceding paragraphs wherein statistical post processing is used to interpret the potential and current measurements and thus provide an output indicative of the tendency for the metal surface to undergo localized corrosion.

The present invention also contemplates a method according to the aforesaid paragraphs wherein domain transform analysis post processing is used to interpret the potential and current measurements and thus provide an output indicative of the tendency for the metal surface to undergo localized corrosion. The techniques of domain transform include, but are not limited to, FFT, Laplace transforms, Z transforms, and wavelet analysis.

The present invention also contemplates a method according to the aforesaid paragraphs wherein pattern recognition is used to provide a means for detecting metastable pitting events, and subsequent processing is used to provide an output indicative of the tendency for the metal surface to undergo localized corrosion.

The present invention further includes an apparatus for detecting the tendency of a material surface to undergo localized corrosion, comprising a working electrode and a second electrode made from substantially the same material (and at the same surface state) as the material surface, a reference electrode, a means for biasing the working electrode anodically with respect to the second electrode, a means for measuring the current between the working and second electrodes, a means for measuring the potential between the working electrode and the reference electrode, and means for analyzing the signals produced to yield a signal indicative of the tendency for the metal surface to undergo localized corrosion.

In addition, the present invention alternatively provides an apparatus for detecting the tendency of a material surface to undergo localized corrosion, comprising a working electrode made from substantially the same material (and at the same surface state) as the material surface, a reference electrode, a means for biasing the working electrode anodically with respect to the material surface, a means for measuring the current between the working electrode and material surface, a means for measuring the potential between the working electrode and the reference electrode, and a means for analyzing the signals produced to yield a signal indicative of the tendency for the metal surface to undergo localized corrosion.

The invention further contemplates apparatus as described by either of the two paragraphs above, further comprising means for providing statistical post-processing to extract the mean, standard deviation, rms, and other statistical values from the current and potential measurements and further analyzing and/or comparing these values to provide an output which is indicative of the tendency of the metal surface to undergo pitting corrosion.

The invention further contemplates apparatus as described by either of the two aforementioned paragraphs, further comprising means for domain transform analysis post processing which is used to interpret the potential and current measurements and thus provide an output indicative of the tendency for the metal surface to undergo localized corrosion. The techniques of domain transform include, but are not limited to, FFT, Laplace transforms, Z transforms, and wavelet analysis.

The invention further contemplates apparatus as described by either of the two aforementioned paragraphs, further comprising means for providing alternating current (AC) post-processing to decompose the current and potential signals into spectra where average values from various frequency bands are compared to provide an output which is indicative of the tendency of the metal surface to undergo pitting corrosion.

In addition, the invention contemplates apparatus as described by either of the two aforementioned paragraphs, further comprising means for utilizing pattern recognition to identify metastable pitting events in the current and potential signals, and using these events to provide an output proportional to the number of events per unit time, which is indicative of the tendency of the metal surface to undergo pitting corrosion.

DETAILED DESCRIPTION

Figure 1:
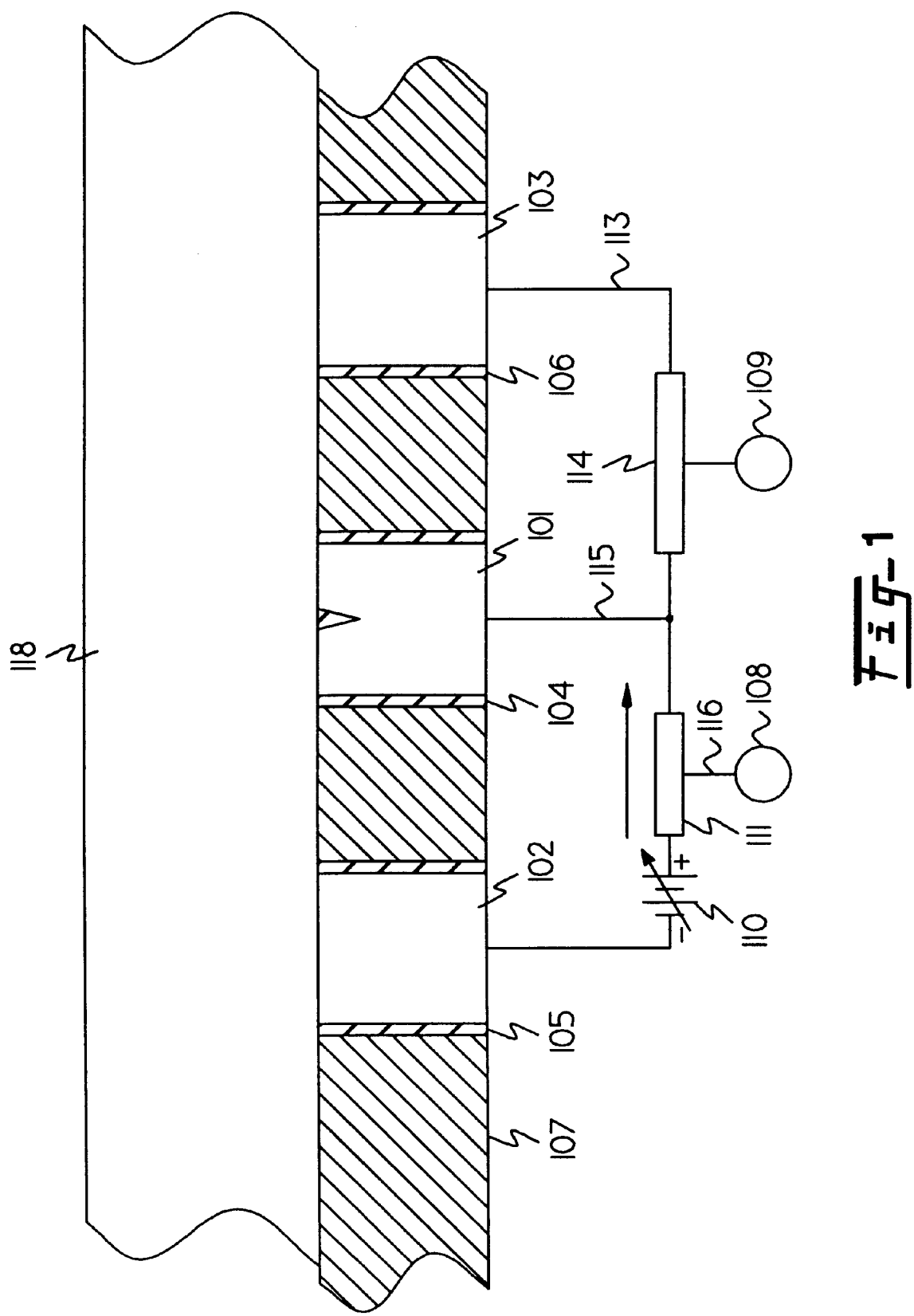
FIG. 1 is a diagrammatic illustration showing two working electrodes and a reference electrode in the wall of a vessel being monitored in accordance with the present invention.

In accordance with the present invention, one or two working electrodes are provided, as well as a reference electrode. The biasing of a working electrode provides the unique advantages of the present invention. The introduction of the bias causes anodic processes to be encouraged on one electrode while cathodic processes are encouraged on the other, while the ensemble is free to evolve with time. As an immediate benefit, more of the current due to pit formation is measured, which improves sensitivity. Annihilation of pitting events, wherein pitting events take place simultaneously on both electrodes, is discouraged.

Still another benefit is that the anode, though physically identical to the cathode, is sensitized to pitting corrosion. The invention therefore has the ability to detect the onset of pitting corrosion at very low levels. In accordance herewith, this is accomplished by polarizing the working electrodes. By adjusting the level of anodic polarization at one of the electrodes, the pitting corrosion can be seen earlier than with other known methods, before it does critical damage to the metal surface being monitored.

Installing The Electrodes And Adjusting The Bias Voltage

The installation and adjustment of the physical and electrical operating parameters of the working electrodes will now be presented.

The voltage source for biasing the working electrodes can come from a battery with a resistive divider across it. Alternatively the voltage source may include a commercial regulated supply with a potentiometer divider to adjust the bias value.

The working electrodes should normally be between 1 and 50 $cm^2$ in exposed area. Too small an area may not provide a sufficient quantity of surface defects for nucleation of pits, resulting in a test electrode that does not represent the surface being tested. Electrodes having a larger area may be inconsistent with the geometry of the structure being monitored and disrupt fluid flow patterns in it. A circular cross section is preferred but other geometries will work as well. In one implementation, the working electrodes are spaced apart about the same distance as their size.

Inserting and sealing the working electrodes in the vessel or chamber being monitored is a critical procedure. At the point of sealing the electrodes in the vessel being tested, the possibility of crevice corrosion exists and should be avoided by careful insertion techniques. If crevice corrosion takes place at the site of electrode insertion, error in the pitting corrosion readings may result.

Desirably, the working electrodes are chemically bonded within the vessel being monitored. To avoid crevice corrosion, it is preferable to use crevice-free washers rather than o-rings if a mechanical seal is used.

In most cases, the reference electrode is a pseudo-reference consisting of another piece of the same material as the surface being tested. This is a well accepted strategy for reference electrodes in field probes. Alternatively, the reference can be either a piece of a more inert metal such as Inconel or platinum or it can be a field version of a laboratory reference electrode such as the Ag/AgCl reference or the SCE (saturated calomel electrode).

A number of considerations concern the methods for adjusting the bias voltage to obtain optimum results. The bias voltage applied may generally be between 25 millivolts and one volt. Lower voltages are generally preferable to higher voltages. If the applied voltage is too high, it may excessively accelerate the corrosion in progress at the electrodes. Too high a bias potential may cause the potential to exceed the critical breakdown potential of the electrode, causing runaway general corrosion.

The bias voltage applied in accordance with the present invention is selected to correspond with the corrosive fluid in the process underway and the electrochemical characteristics of the metal under test. There are at least two methods that can be used to determine the correct bias.

The first involves use of a standard laboratory corrosion test. A model of the system to be monitored is assembled in a laboratory electrochemical test cell. The model should be in a condition where no pitting corrosion occurs. The corrosive medium (including any corrosion inhibitors) and electrode material used must correspond as closely as possible to those in the system to be monitored. A cyclic polarization test is run to determine the critical repassivation potential of the system. At this potential, measured versus the open circuit potential of the electrode, pits, once formed in the material, will repassivate. The bias potential used in the field monitor is set to this value minus 50 mV. At this potential, pitting is not expected to occur unless the system is upset in some way. The cyclic polarization test methods are described in "Pitting" by Robert G. Kelly, Chapter 18, *Corrosion Tests and Standards: Application and Interpretation, MNL* 20, American Society for Testing and Materials (1995).

The second method to determine the correct bias potential can be performed either using a probe in the actual system under test or using a laboratory model of the system. It requires that the system (or model) be placed in a condition in which some metastable pitting occurs. One way to achieve this condition is temporary operation of the system without any corrosion inhibitor.

One begins at a bias potential of about zero. At this bias potential the biased ZRA's current output should show electrochemical noise signals in both anodic and cathodic directions. Then the bias voltage is raised until only positive (anodic) pulses are seen in the current from the anodically biased working electrode.

Prior to this adjustment period, take care to allow time for stabilization. The passive film that naturally forms on the electrodes must be allowed to grow until it resembles that on the metal surface being monitored.

Typically a 50 millivolt (mV) voltage bias (versus the open circuit potential) is useful to use with stainless steel metal. As confirmed by tests at The Pennsylvania State University using the methods taught herein, a reasonable point at which to start in determining the optimum bias voltage is 25 mV.

The optimal voltage may be different for each chemical system of metal and corrosive medium. That is to say, where an optimal voltage for a system has been determined and then the fluid is modified in concentration or composition, there may be a change in the bias voltage that should be applied in accordance with the present invention to yield the most sensitive reading. Experience will indicate what bias voltage produces the best performance. This optimal bias potential may vary with factors such as the metal sample, the type and concentration of the corrosive fluid to which the metal and the working electrodes are exposed, the velocity of the fluid movement, the presence of welds, mechanical stress, and the regime of the fluid flow between laminar and turbulent.

The present invention provides meaningful data for a wide range of materials that are susceptible to corrosion. A nonexhaustive list includes stainless steel, aluminum, titanium, super alloy steels, welded segments, and even germanium as used in infrared sensors. The present invention should perform and give good results with a wide range of corrosive fluids with a broad range of concentrations.

Turning now to the drawings, a preferred embodiment of the invention is shown in FIG. 1. The three electrodes 101, 102 and 103 are embedded in the metallic wall 107 of a vessel being monitored, that contains liquid 118. Each of the electrodes 101, 102 and 103 is electrically insulated from the wall 107 by an insulator 104, 105 and 106, respectively.

The lead 113 from the reference electrode 103 is connected to a differential electrometer 114 with the return electrometer lead 115 connected to the anodically biased electrode 101. This provides the voltage signal 109 that will be analyzed along with the current signal 108 as described below. Current signal 108 is provided through line 116.

A zero-resistance ammeter ("ZRA") 111 is connected to the anodically biased electrode 101 and to the positive side of the DC bias voltage 110 with the negative side of the bias voltage connected to the cathodically biased electrode 102.

Figure 2:
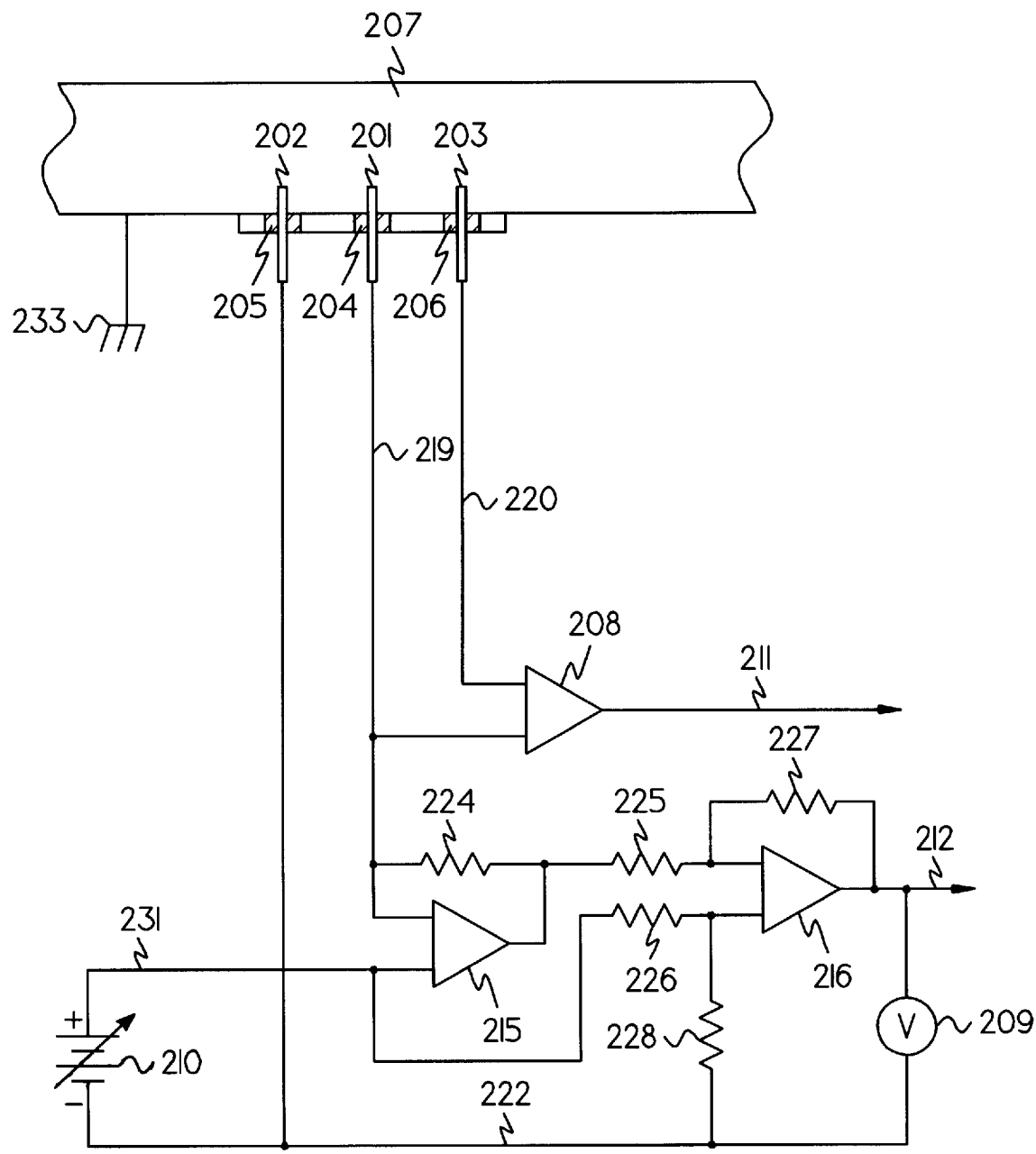
FIG. 2 is a diagram of a circuit providing current and voltage output from the three electrodes as in FIG. 1.

The electronic circuit implementation of FIG. 1 is shown in FIG. 2. The biased ZRA is configured as an operational amplifier 215 wired to provide current-to-voltage conversion followed by differential amplifier 216. This results in the current signal output 212. The bias voltage 210 is adjustable and provides a DC voltage between the grounded second electrode 202 and the operational amplifier circuit 215. The current signal 212 is provided for analysis, along with the voltage signal 211 that is developed as described above.

FIG. 2 shows a diagram of a three-electrode embodiment of the present invention. In FIG. 2, the negative end of bias voltage source 210 is connected to instrument ground 222, and the positive end of bias voltage source 210 is connected via conductor 231 to operational amplifier 215 and thence via conductor 219 to electrode 201. Working electrodes 201 and 202 and reference electrode 203 are each insulated from the grounded vessel wall 207 by insulators 204, 205 and 206, respectively. Vessel wall 207 is grounded through grounding strap 233. Signals from reference electrode 203 are conveyed by conductor 220 to differential electrometer 208 which is connected across conductors 219 and 220. The output of differential electrometer 208 is applied to conductor 211. Resistor 224 is connected between conductor 219 and the output of operational amplifier 215. The output of operational amplifier 215 is also connected via resistor 225 to input one of differential amplifier 216. The positive end of bias voltage source 210 is connected to the second input of differential amplifier 216 via resistor 226. The second input of differential amplifier 216 is grounded via resistor 228. The output of differential amplifier 216 is connected to input one via resistor 227, to voltmeter 209 and is applied to conductor 212. Voltmeter 209 is connected across the output of differential amplifier 216 and instrument ground 222.

In accordance with the present invention, such a three-electrode array may be replicated and installed at additional points in the system. Numerous points in the operating system that may be suspect can thereby be monitored for pitting corrosion.

Figure 3:
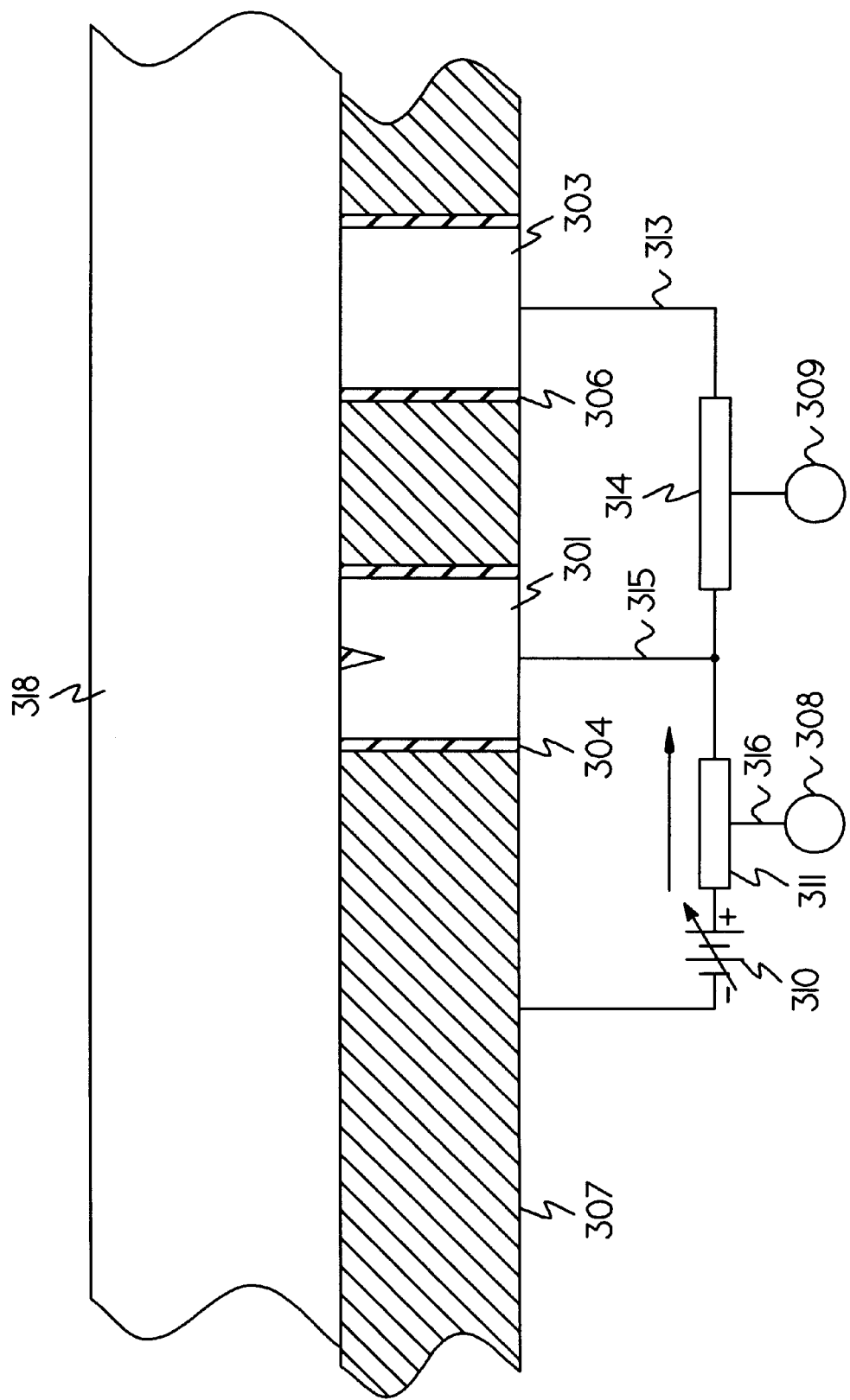
FIG. 3 is a diagrammatic illustration showing two electrodes in the wall of vessel being monitored in an alternate embodiment of the present invention.
Figure 4:
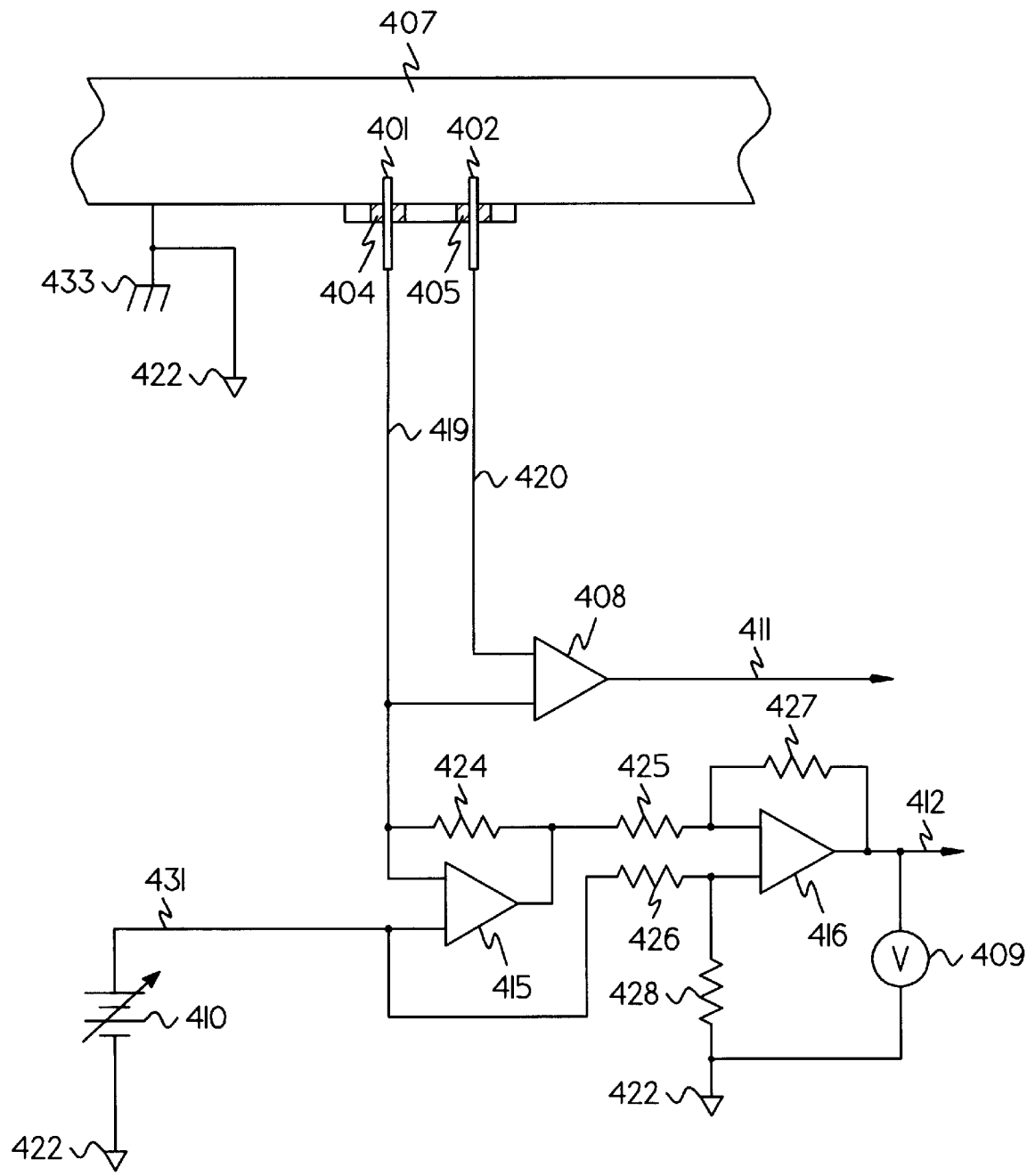
FIG. 4 is a diagram of a circuit providing current and voltage output from the two electrodes as in FIG. 3.

FIGS. 3 and 4 show another embodiment of the invention. In this embodiment, two electrodes are fabricated and mounted in the wall of the working vessel. The wall of the vessel takes the place of the cathodically biased electrode in the previous embodiment. In this instance the working electrode 301 in FIG. 3 provides the input to the biased ZRA. The biased circuit ZRA provides the current data stream for analysis. The potential data stream is obtained from the working electrode 301 and reference electrode 303 via the differential electrometer 314. FIG. 4 demonstrates that the same circuit can be used for both embodiments of the invention, with only a change in the ground connections.

FIG. 3 shows an embodiment of the invention in which working electrode 301 and reference electrode 303 are fabricated and mounted in wall 307 of the working vessel that contains liquid 318. In this embodiment the working electrode 301 in FIG. 3 provides one input to the ZRA loop while the return conductor is directly connected to the vessel wall 307. The ZRA loop provides the current data stream for analysis. The potential data stream is obtained from the working electrodes 301 and reference electrode 303 via the electrometer 314 via voltmeter 309. Insulators 304 and 306 correspond, respectively, to insulators 104 and 106 of FIG. 1. The bias voltage source 310 is connected to the vessel wall 307 and a ZRA 311. The lead 313 from the reference electrode 303 is connected to a differential electrometer 314 with the return electrometer lead 315 connected to the anodically biased electrode 301. This provides the voltage signal 309 that will be analyzed along with the current signal 308, provided through line 316 from ZRA 311.

FIG. 4 shows a diagram of a two-electrode embodiment of the present invention. In FIG. 4, the negative end of bias voltage source 410 is grounded and the positive end of bias voltage source 410 is connected via conductor 431 to operational amplifier 415 and thence via conductor 419 to electrode 401. Reference electrode 402 and electrode 401 are insulated from the grounded vessel wall 407 by insulators 404 and 405 respectively. Signals from reference electrode 402 are conveyed by conductor 420 to differential electrometer 408 which is connected across conductors 419 and 420. The output of differential electrometer 408 is applied to conductor 411. Resistor 424 is connected between conductor 419 and the output of operational amplifier 415. The output of operational amplifier 415 is also connected via resistor 425 to the first input of differential amplifier 416. The positive end of bias voltage source 410 is connected to the second input of differential amplifier 416 via resistor 426. The second input of differential amplifier 416 is grounded via resistor 428. The output of differential amplifier 416 is connected to the first input of differential amplifier 416 via resistor 427 and is applied to conductor 412. Voltmeter 409 is connected across the output of differential amplifier 416 and instrument ground 422 which is tied to system ground 433.

The current and potential data streams developed above can be analyzed by any of various known techniques or combinations thereof to provide information on the type and rate of corrosion taking place on the metal surface being monitored.

Time-series analysis

One method for developing data for corrosion involves a time series analysis of the potential and current data streams. This involves any of the following:

calculating a real-time RMS current and/or potential, $$V_{rms}(t) = \sqrt{\frac{\int_{t-\tau}^{t} V(x)^2 dx}{\tau}} \quad \text{(continuous form)}$$

$$V_{rms}[i] = \sqrt{\frac{\sum_{i-N+1}^{i} V[k]^2}{N}} \quad \text{(discrete form)}$$

calculating a real-time mean current and/or potential, $$\overline{V}(t) = \frac{\int_{t-\tau}^{t} V(x)dx}{\tau} \quad \text{(continuous form)}$$

$$\overline{V}[i] = \frac{\sum_{i-N+1}^{i} C[k]}{N} \quad \text{(discrete form)}$$

(The lag time, $\tau$, in the continuous case and the sample rate and summation limit, N, are variable in the discrete case.)

calculating a standard deviation or population standard deviation, $$V_{sd}(t) = \sqrt{\frac{\int_{t-\tau}^{t} (V(x) - \overline{V}(x))^2 dx}{\tau}} \quad \text{(continuous form)}$$

$$V_{sd}[i] = \sqrt{\frac{\sum_{i-N+1}^{i} (V[k] - \overline{V}[k])^2}{N}} \quad \text{(discrete form)}$$

calculating a regression residual where $V_{bf}$ is a best fit value, $$V_{resid}(t) = \sqrt{\frac{\int_{t-\tau}^{t}(V(x)-V_{bf}(x))^2 dx}{\tau}} \quad \text{(continuous form)}$$

$$V_{resid}[i] = \sqrt{\frac{\sum_{i-N+1}^{i}(V[k]-V_{bf}[k])^2}{N}} \quad \text{(discrete form)}$$

applying various forms of digital or analog filtering or windowing to remove extraneous noise from the data stream and calculation of Fourier Transform or other transforms (including but not limited to the Z transform, Laplace transform, wavelet analysis, or calculation of power spectral densities followed by frequency domain calculations), then transforming the results back to the time domain.

Alternatively one may apply any combination of the above in any order to yield signals indicative of pitting corrosion and general corrosion.

Pattern recognition analysis

There is another class of approaches to data analysis which can be used in accordance with the present invention to produce pitting tendency data. FIG. 5 shows pitting traces where the events, although microscopic in extent, are easily identifiable and countable.

Figure 5A:
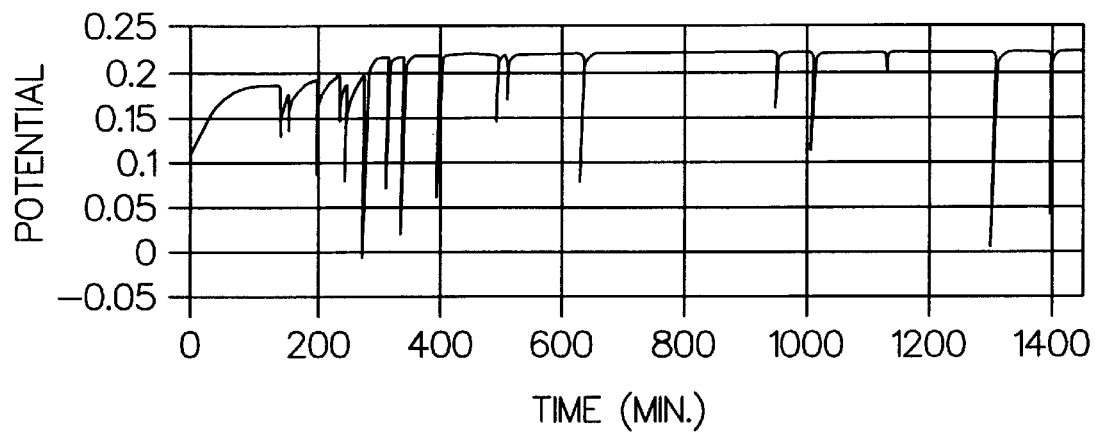
FIGS. 5a and 5b shows potential and current versus time curves in accordance with the present invention, of a system undergoing metastable pitting.
Figure 5B:
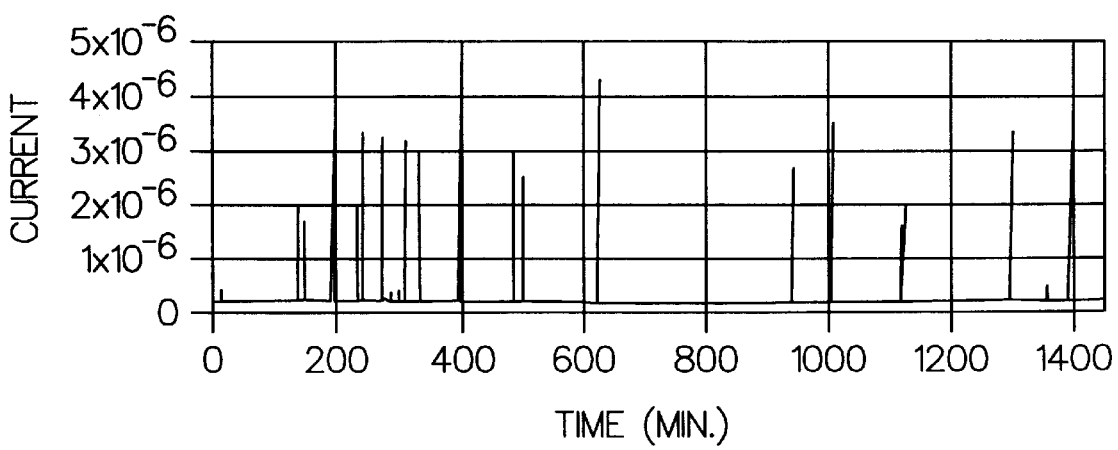

FIGS. 5a and 5b show graphs that illustrate potential and current events versus time curves as measured by a LCMA of the present invention. FIGS. 5a and 5b show pitting traces where the events, although microscopic in extent, are easily identifiable and countable. FIG. 5a shows a graph of potential in volts on the Y-axis and time in minutes on the X-axis. The trace shown in FIG. 5a represents negative-going voltage pulses that are measured by a LCMA of the present invention when monitoring a system undergoing metastable pitting. FIG. 5b shows a graph of current in microamps on the Y-axis and time in minutes on the X-axis. The trace shown in FIG. 5b represents positive-going current pulses that are measured by a LCMA of the present invention when monitoring a system undergoing metastable pitting.

In one particular implementation, a device counts pitting events per unit time, indicating the rate of corrosion in direct proportion.

Figure 6:
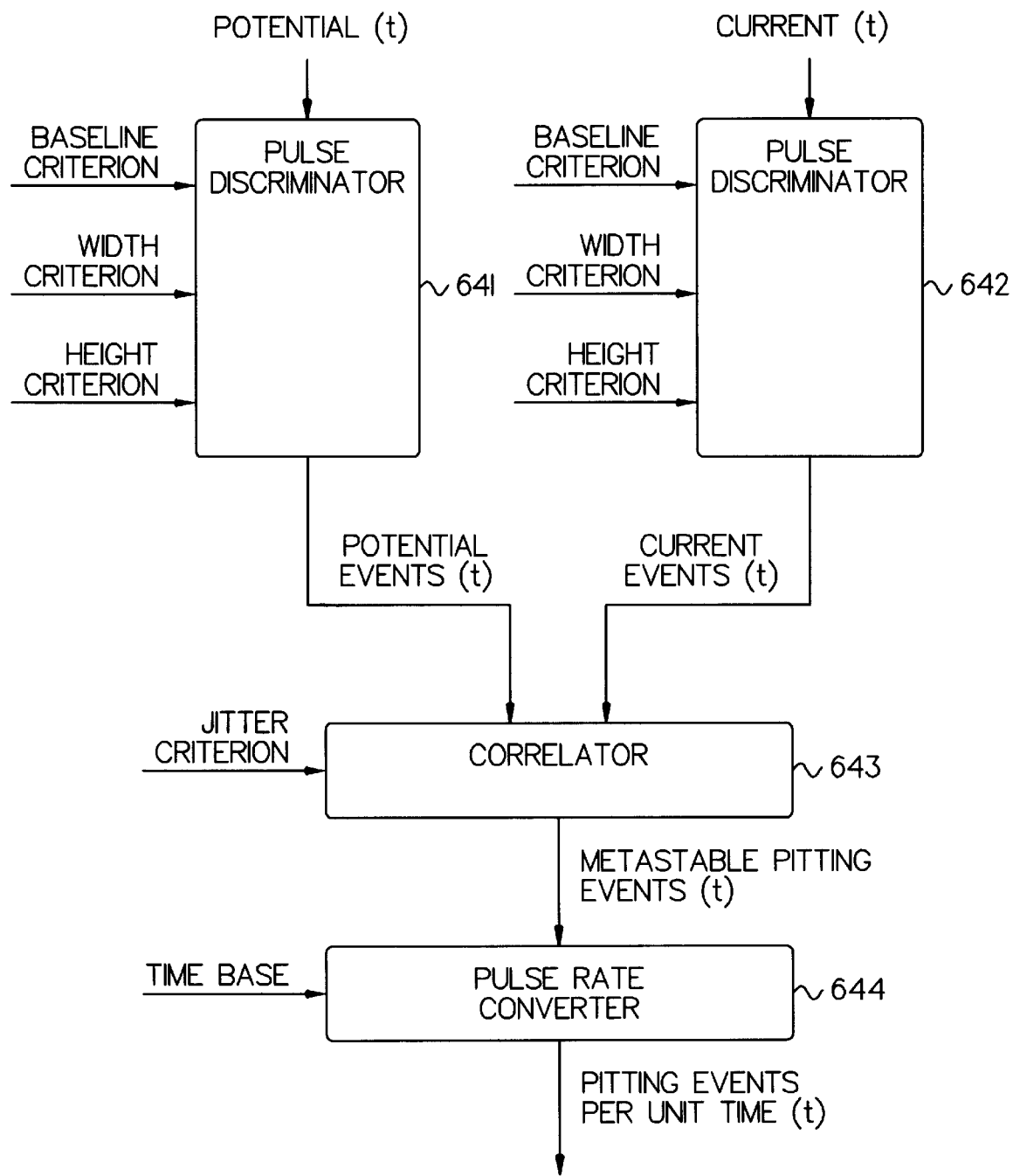
FIG. 6 is a diagram of one possible algorithm for pattern recognition of pitting transients.

FIG. 6 illustrates one approach to such an analysis. Other pattern recognition approaches are possible. FIG. 6 is a flow-chart diagram that illustrates an algorithm for pattern recognition of pitting transients, other suitable analytical processes will be known to those of skill in the art. As shown in FIG. 6, pulse discriminator 641 receives an input of voltage signals from a LCMA of the present invention and is adjustable in respect to voltage baseline, voltage pulse width and voltage pulse height. Pulse discriminator 641 removes the baseline and selects voltage pulses that fit the pre-set width and height criteria for potential pulses.

Pulse discriminator 642 receives input of current signals from a LCMA of the present invention and is adjustable in respect to current baseline, width of current pulses and height current pulses. Pulse discriminator 642 removes the baseline and selects pulses that fit the pre-set width and height criteria for current pulses. Pulse discriminators 641 and 642 pass their respective potential event and current event outputs to correlator 643. Correlator 643 is adjustable for a "jitter criterion" which permits adjustment of a criterion concerning the degree of coincidentality of potential and current pulses. Correlator 643 selects coincident potential and current events and discards current pulses that are not coincident with potential pulses and potential pulses that are not coincident with current pulses. Correlator 643 passes signals corresponding to coincident potential and current events, i.e., metastable pitting events, to pulse rate converter 644. The time base of pulse rate converter 644 is adjustable, and it provides an output in terms of pitting events per unit time.

Other methods

Within the scope of the present invention, other approaches to signal interpretation may be used. For example, one could combine the time-series and pattern recognition approaches.

The description herein of specific methods and apparatus are illustrative and does not imply exclusion of numerous other arrangements that one skilled in the art might configure and employ in accordance with the present invention.

What is claimed is:

1. Apparatus for detecting localized corrosion of a material surface, comprising:

(a) a first electrode having a surface of substantially the same composition and state as a material surface;

(b) a second electrode; and (c) a reference electrode;

wherein said material surface and said electrodes are exposed to an environment;

(d) means for anodically biasing said first electrode with respect to said second electrode;

(e) means for producing a first signal representing the current flowing between said first electrode and said second electrode;

(f) means for producing a second signal representing the potential between said first electrode and said reference electrode; and (g) means for processing said first signal and said second signal to yield an output signal indicative of the degree of localized corrosion occurring at the material surface.

2. The apparatus of claim 1, wherein:

said means for producing said first signal representing the current flowing between said first electrode and said second electrode comprises:

an I/E converter and a differential amplifier, connected through a common system ground.

3. The apparatus of claim 1, wherein:

said means for producing said second signal representing the potential between said first electrode and said reference electrode comprises a differential electrometer.

4. The apparatus of claim 1 wherein:

said second electrode is said material surface.

5. The apparatus of claim 1 wherein:

said second electrode is an electrode having a surface of substantially the same composition and state as said material surface.

6. The apparatus of claim 1 wherein:

said reference electrode is an inert metal, a silver/silver chloride reference electrode, a standard calomel electrode, or a material having a surface of substantially the same composition and state as said material surface.

7. The apparatus of claim 1, wherein said means for processing said first signal and said second signal comprises means for performing statistical post-processing, thereby providing an output which is indicative of the degree of localized corrosion occurring at the material surface.

8. The apparatus of claim 1, wherein said means for processing said first signal and said second signal comprises means for domain transform analysis post processing, thereby providing an output which is indicative of the degree of localized corrosion occurring at the material surface.

9. The apparatus of claim 1, wherein said means for processing said first signal and said second signal comprises means for utilizing pattern recognition to identify metastable pitting events in said first signal and said second signal, and means to provide an output proportional to the number of events per unit time, thereby providing an output which is indicative of the degree of localized corrosion occurring at the material surface.

10. A method for detecting localized corrosion of a material surface exposed to an environment comprising the steps of:

(a) providing an anodically biased electrode and a cathodically biased electrode having surfaces of substantially the same composition as the material surface and a reference electrode;

(b) exposing said electrodes to the same environment as the material surface;

(c) producing a first signal that represents the current flowing between said anodically biased electrode and said cathodically biased electrode;

(d) producing a second signal that represents the potential between said anodically biased electrode and said reference electrode; and (e) processing said first signal and said second signal to yield an output signal indicative of the degree of localized corrosion occurring at the material surface.

11. A method of claim 10 wherein:

statistical post processing is used to process the first signal and the second signal.

12. A method of claim 10 wherein:

domain transform analysis post processing is used to process said first signal and said second signal.

13. A method of claim 10 wherein:

pattern recognition post processing is used to process said first signal and said second signal.

14. A method for detecting localized corrosion of a material surface exposed to an environment, comprising the steps of:

(a) providing a working electrode to be anodically biased, having a surface of substantially the same composition and surface state as the material surface;

(b) providing a reference electrode;

(c) exposing said electrodes to the same environment as the material surface;

(d) applying an anodic bias with respect to the material surface to said working electrode;

(e) producing a first signal that represents the current flowing between said working electrode and said material surface;

(f) producing a second signal that represents the potential between said working electrode and said reference electrode; and (g) processing said first signal and said second signal to produce an output indicative of the degree of localized corrosion occurring at the material surface.

15. A method of claim 14 wherein:

statistical post processing is used to process the first signal and the second signal.

16. A method of claim 14 wherein:

domain transform analysis post processing is used to process said first signal and said second signal.

17. A method of claim 14 wherein:

pattern recognition post processing is used to process said first signal and said second signal.

* * * * *